US006350275B1

(12) United States Patent
Vreman et al.

(10) Patent No.: US 6,350,275 B1
(45) Date of Patent: Feb. 26, 2002

(54) DEVICES FOR TREATING CIRCADIAN RHYTHM DISORDERS USING LED'S

(75) Inventors: Hendrik J. Vreman; David K. Stevenson, both of Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/094,231

(22) Filed: Jun. 9, 1998

Related U.S. Application Data (60) Provisional application No. 60/049,230, filed on Jun. 9, 1997.

(51) Int. Cl.[7] ............................................... A61N 5/06
(52) U.S. Cl. ........................................... 607/88; 607/91
(58) Field of Search ....................... 607/88–92; 606/27, 606/33; 351/200, 203

(56) References Cited

U.S. PATENT DOCUMENTS

| | | | |
|---|---|---|---|
| 4,516,110 A | * 5/1985 | Overmyer | 340/323 |
| 4,858,609 A | 8/1989 | Cole | |
| 4,911,166 A | 3/1990 | Leighton et al. | |
| 5,163,426 A | 11/1992 | Czeisler et al. | |
| 5,358,503 A | * 10/1994 | Bertwell et al. | 606/27 |
| 5,447,528 A | * 9/1995 | Gerardo | 607/88 |
| 5,503,637 A | 4/1996 | Kyricos et al. | |
| 5,616,140 A | * 4/1997 | Prescott | 606/10 |
| 5,709,645 A | * 1/1998 | Siever | 600/27 |
| 5,793,405 A | * 8/1998 | Shakuda | 347/238 |
| 5,805,267 A | * 9/1998 | Goldman | 351/203 |
| 5,862,167 A | * 1/1999 | Sassa et al. | 372/45 |
| 5,913,883 A | * 6/1999 | Alexander et al. | 607/88 |
| 5,977,566 A | * 11/1999 | Okazaki et al. | 257/99 |
| 6,053,936 A | * 4/2000 | Koyama et al. | 607/88 |
| 6,135,117 A | * 10/2000 | Campbell et al. | 128/898 |

* cited by examiner

Primary Examiner—Roy Gibson
(74) Attorney, Agent, or Firm—Lumen Intellectual Property Services, Inc.

(57) ABSTRACT

A device is provided for treating a circadian rhythm disorder in a subject. The device includes a plurality of light emitting diodes (LED's), preferably blue to green; a mounting to which the LED's are connected: a material for positioning the LED's within 3 cm of the subject, with an orientation toward the subject; a portable power supply electrically connected to the LED's; and a control connected to the LED's for altering the operation of the LED's. The device is sufficiently light and compact to be comfortably worn by the subject. One or more such devices are used to deliver light to a subject's retinas, to the subject's vascular tissue, or simultaneously to both the retinas and the vascular tissue. For illumination of the retina, small chip-type LED's are integrated into the frames of eyeglasses and positioned to direct light into the eyes of the subject. For illumination of the vascular tissue, an array of lens or chip type LED's are contained in a casing that is secured against the skin of the subject. The devices can be used independently of each other, or can be used in combination for more effective and/or flexible treatment.

12 Claims, 5 Drawing Sheets

DEVICES FOR TREATING CIRCADIAN RHYTHM DISORDERS USING LED'S

This application is related to U.S. patent application Ser. No. 08/824,631, entitled "Phototherapy of Jaundiced Newborns Using Semiconductor Light-Emitting Devices (LED's)," filed Mar. 27, 1997, which is herein incorporated by reference. This application claims priority from U.S. Provisional Patent Application No. 60/049,230, entitled "Phototherapy for Seasonal Affective Disorder (SAD) Using LED's", filed Jun. 9, 1997, which is herein incorporated by reference.

FIELD OF THE INVENTION

This invention relates to the field of methods and devices for phototherapy. More particularly, the invention relates to methods and devices for treating and preventing circadian rhythm disorders such as seasonal affective disorder (SAD), jet lag, and related conditions using light emitting diodes (LED's).

BACKGROUND

Circadian rhythms are physiological and behavioral oscillations that are normally synchronized with the natural light-dark cycle of the day. Circadian rhythm disorders are inappropriate or undesired circadian rhythms. Such disorders typically are related to sudden and/or extreme changes in the relationship between an organism's exposure to environmental light and its activity. For example, circadian rhythm disorders are known to be associated with change in geographical location (jet lag) and night activity (graveyard shift workers). Another common type of circadian rhythm disorder is seasonal affective disorder (SAD), which is characterized by symptoms such as depression during the winter seasons when the duration of daylight is reduced.

It has long been known that circadian rhythms in humans and other mammals are affected by exposure of the retina to light. Accordingly, various techniques and devices have been developed to treat circadian rhythm disorders by exposing the eyes to light.

In U.S. Pat. No. 4,858,609 Cole discloses a bright light mask for shining high intensity light into a subject's eyes at preselected time periods to modify circadian rhythms, even while the subject is asleep. Light from an incandescent bulb or a bank of green LED's is delivered through optical fibers to the mask, providing to the eyes an intensity of at least 2000 lux and a wavelength in the range of 500 to 600 nm. A computer controller determines the intensity and timing of the light. The device of Cole, however, is not portable, blocks the subjects vision, and is expensive.

Czeisler et al. in U.S. Pat. No. 5,163,426 disclose techniques for assessing and adjusting circadian phase using goggle-like devices, powered by an external power supply. The goggles expose the retinas of a subject to high intensity light generated by fluorescent or incandescent lamps positioned near the eyes The goggles, however, interfere with normal vision, are not completely portable, are expensive, and are fragile.

In U.S. Pat. No. 5,503,637 Kyricos et al. disclose a portable apparatus for producing and delivering high-intensity white light to the eyes in order to modify the subject's circadian phase. The apparatus is shown in the form of a sports visor having a high intensity cold cathode fluorescent lamp imbedded in the underside The light is filtered so that unwanted frequencies of light are not radiated to the subject's face. A controller is provided which is programmed to deliver an amount of light determined to treat a circadian rhythm disorder. The apparatus, however, is fragile, bulky, expensive, and cannot be used while asleep, with eyes closed, or without attracting attention.

In U.S. Pat. No. 4,911,166 Leighton et al. disclose a device for delivering high intensity light to a patient's eyes for treating SAD and the like. It has a high intensity halogen or other incandescent bulb, with reflective optics to direct a large portion of the light directly into the subject's eyes. The light source is fixed to a head-mounted apparatus. The apparatus, however, is fragile, bulky, interferes with normal vision, and cannot be used without attracting attention.

Known techniques for treating circadian rhythm disorders, therefore, suffer from one or more of the following disadvantages: they are expensive, fragile, bulky, not portable, energy inefficient, emit unwanted heat and/or radiation, interfere with normal vision, and may attract undesired attention from others. It should be emphasized that all these devices for treating circadian rhythm disorders are based on the exposure of the retina to light, usually broad spectrum (white) light.

In the article "Extraocular Circadian Phototransduction" (*Science*, Vol. 279, Jan. 16, 1998) Scott S. Campbell and Patricia J. Murphy teach that circadian rhythms can be altered by illuminating the popliteal area of each leg (i.e., the area behind the knee). Campbell and Murphy use a commercially available device which has a halogen lamp in a metal housing with a fan to dissipate heat. A collection of 2400 optical fibers are used to deliver the light from the housing to a 10 cm×15 cm×0.5 cm pad. The pad is held in place behind the knee by a polyester athletic knee brace for 3 hours. The wavelength of the light delivered to the subject by the device is in the 455 nm to 540 nm range, i.e. blue-green light. They also teach the use of white light from a fluorescent lamp. This device, So however, has several disadvantages: it is not portable, it is awkward, it generates considerable heat and noise, it consumes considerable power, and is very expensive. In addition, their use of the popliteal area interferes with normal activity and comfort since it limits the bending of the knee.

SUMMARY OF THE INVENTION

In view of the above, it is an object of the present invention to provide a device for effectively treating circadian rhythm disorders that is inexpensive, portable, durable, compact, light-weight, energy efficient, does not generate undesired heat or radiation, does not interfere with normal vision, and inconspicuous. It is another object of the present invention to provide a device for treating circadian rhythm disorders that may be used while the subject is asleep as well as awake.

Another object of the invention is to provide such a device having precise control and delivery of specific wavelengths and intensities of light to the subject.

The above objects and advantages are achieved through the use of devices that deliver light to a subject's retinas, to the subject's vascular tissue, or simultaneously to both the retinas and the vascular tissue. The vascular tissue is typically the vascular bed underlying the skin. The portable devices employ one or more LED's for directly illuminating the retinas and/or vascular tissue of the subject. The LED's may be single LED's, LED arrays, or integrated array LED chips. For illumination of the retina, one or more small LED's are placed into the frames of eyeglasses and positioned to direct light into the eyes of the subject. For illumination of the vascular tissue, an array of LED's are contained in a casing that is secured against the skin of the subject. The devices are preferably powered by separate batteries. Alternatively the devices can be powered by a common battery supply. The devices can be used independently of each other, or can be used in conjunction for more effective and/or flexible treatment. In a preferred embodiment, the intensity, timing, and wavelengths of light delivered by the devices is easily adjusted by controls on the device. wavelength selectivity provides fine-tuning of the most appropriate treatment for the condition of the subject.

In one aspect of the invention, a device is provided for treating a circadian rhythm disorder in a subject. The device comprises one or more light emitting diodes (LED's), preferably blue to green in color; a mounting to which the LED's are connected; a material for positioning the LED's within 3 cm of the subject, with an orientation toward the subject; a portable power supply electrically connected to the LED's; and a control connected to the LED's for altering the operation of the LED's. The device is sufficiently light and compact to be comfortably worn by the subject. In one embodiment, the material for positioning the LED's within 3 cm of the subject comprises eyeglass frames and arms, and the LED's are oriented toward the eyes of the subject. In another embodiment, the material for positioning the LED's within 3 cm of the subject comprises a fabric that may be wrapped around a portion of the subject, and the LED's are oriented toward the skin of the subject. The device may also include an integrated circuit for controlling the LED's.

In another aspect of the invention, a method is provided for treating circadian rhythm disorders experienced by a subject. The method comprises illuminating the subject with light produced by a portable device worn by the subject. The device comprises a plurality of light emitting diodes (LED's) positioned within 3 cm of the subject for illuminating the subject, a power supply connected to the LED's, and a control connected to the LED's. The method may further comprise simultaneously illuminating the subject with light produced by an additional device worn by the subject. The devices may illuminate the eyes of the subject, the vascular tissue of the subject, or both. To illuminate the eyes, the device is worn on the face of the subject. To illuminate the vascular tissue, the device is worn on a portion of the subject's body, such as the head, neck, arm, waist or leg. Although multiple wavelengths may be used, preferably, the light produced by the LED's and used to illuminate the subject has a narrow spectral content in the blue to green portion of the spectrum.

DETAILED DESCRIPTION

The present invention provides an improved device for treating circadian rhythm disorders and SAD by illuminating the eyes and/or vascular tissue of a subject. In a preferred embodiment of the invention, an eyeglass-type device and/or a body pad device is provided with small lens type and/or chip LED's for illuminating retinas and/or vascular tissue of the subject. The device may be used to treat and/or prevent any of the various known forms of circadian rhythm disorders, including jet lag, night shift work and SAD.

The LED's used in the devices in the present invention preferably produce blue to green light, thereby providing the maximal effect with minimal light intensity and power consumption. LED's based on gallium nitride technology emit light from 420 nm (blue) to 575 nm (green). At present, the LED's in this portion of the spectrum can be obtained in various narrow wavelength ranges, each approximately 20 nm–40 nm wide at 50% peak height. Selecting specific wavelength LED's allows for delivery of a narrow spectrum of light with the greatest therapeutic value and the lowest potential side effects. Furthermore, LED's of different wavelengths can be combined for more effective therapy. Also, the light intensity can be easily controlled by the number of LED's used and/or the power applied to the LED's. Small LED's of the same or differing wavelengths can be arranged in densely packed arrays to form high intensity light sources. Because LED's are available with different light delivery angles, the area to be illuminated can be controlled by selecting the most appropriate angle for the application.

The invention enjoys several of its advantages due to its use of LED's to deliver light directly to the subject. The LED's are very small, very durable and long-lasting. As a result, the devices are portable, light-weight, comfortable, easy to use, inexpensive, do not dissipate large amounts of heat or unwanted frequencies of light. LED's deliver a relatively high intensity for their physical size and weight. They also have a relatively low power consumption (100 mW) and little heat (infrared) production. They produce no harmful UV radiation, and have high efficiency (optical output power/electrical input power).

Figure 1:
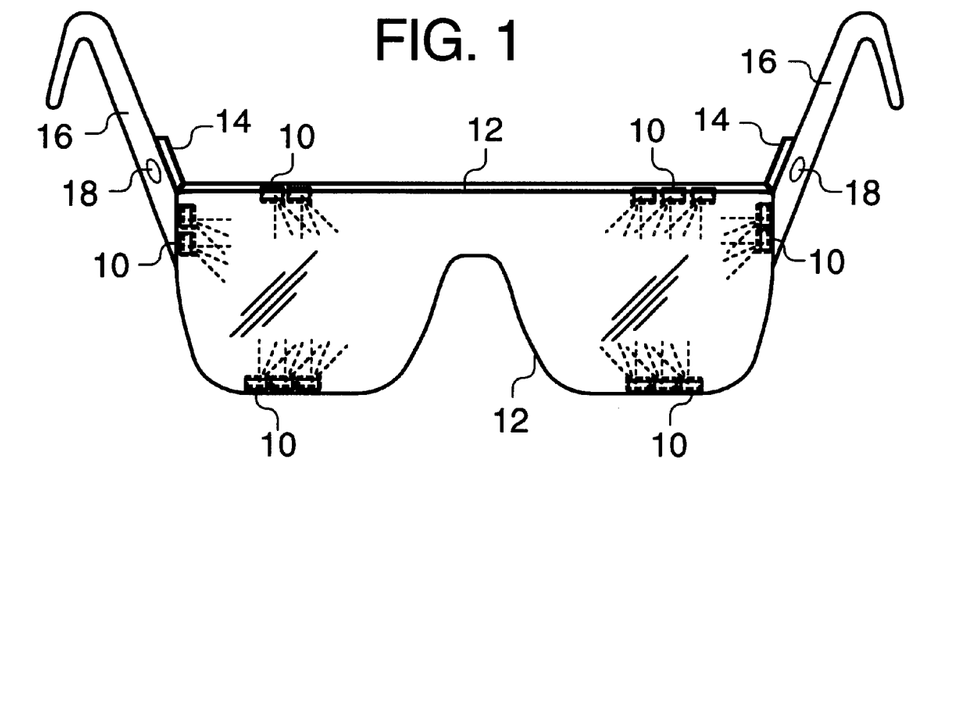
FIG. 1 is a perspective view of an eyeglass device according to the present invention.
Figure 2:
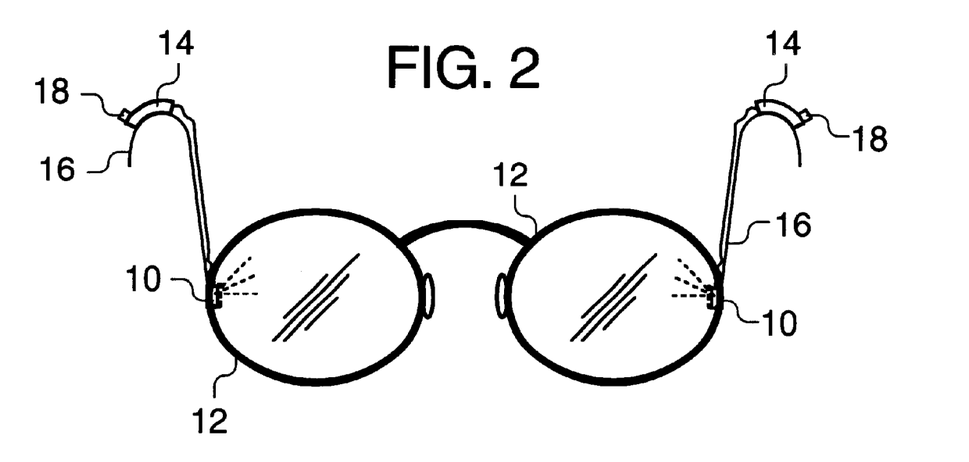
FIG. 2 is a perspective view of an eyeglass device according to the present invention.

FIGS. 1 and 2 show two styles of a portable device according to the present invention. The device uses a plurality of LED's 10 for directly illuminating the retinas of the subject. The LED's used in this embodiment are preferably very small GaN-based chip type LED's with a wavelength in the blue to green portion of the spectrum (e.g., item NSCB 100 or NSCG 100 from Nichia Chemical Industries, Ltd, Tokushima, Japan). These LED's are characterized by superior intensity and efficiency in the blue to green portion of the spectrum. Because these LED's have very high intensity, only one LED per eye may be required, as illustrated in FIG. 2. These LED's are also very compact, having dimensions of only 3 mm×2 mm×1 mm. Thus, several may be used if necessary to provide increased intensity or different wavelengths, as illustrated in FIG. 1. The LED's 10 are built into the frames 12 of eyeglasses, and are positioned to direct light into the eyes of the subject, and may be positioned above, below, and/or to the side of the subject's field of view in the appropriate portion of the frame, as shown. Because the small LED's are integrated into the frame 12, they do not interfere with the subject's normal vision and are inconspicuous. In a preferred embodiment, the direction in which the LED's are pointed may be adjusted by the subject, e.g. by flexibly mounting the LED's, or mounting the LED's on a hinged support integrated into the frame 12. The eyeglasses can have corrective or non-corrective lenses. Safety glasses or frames with no lenses can also serve the same purpose.

The LED's may be powered by small batteries built into the glasses. The batteries (not shown) may be held in a small casing 14 integrated into the arm 16 of the glasses. Alternatively, the batteries may be carried on another part of the body, in which case a thin, flexible power cord connects the batteries to the glasses. Preferably, such a power cord is integrated into the arms of the glasses and passes inconspicuously behind the ear. The batteries are replaceable or rechargeable. Small controls 18, comprising switches, buttons, or dials, for example, are provided in the glasses. These controls 18 are conveniently positioned on the side of the arm 16, allowing the subject to easily adjust the intensity and/or timing of the illumination. A small application-specific integrated circuit (ASIC) or other electronic circuitry housed in the casing 14 controls the activation and timing of the LED's based on input from the controls 18. If multiple different wavelength LED's are built into the glasses, these controls 18 can also adjust the timing and relative intensity of the different wavelength LED's. The intensity of light emitted by the device is determined by the number of LED's which are activated and/or the power applied to the LED's. Preferably, the majority of the LED's emit light in the blue to green range. This wavelength of light is known to be especially effective in the treatment of circadian rhythm disorders.

It will be appreciated that this device provided by the present invention enjoys a combination of many advantages over other devices. The present invention provides a device that is portable, light weight, durable, long-lasting, compact, comfortable, easy to use, inexpensive, effective, energy-efficient, low-voltage, does not consume large amounts of power or dissipate large amounts of heat, does not interfere with vision, and is inconspicuous to wear. In addition, the device provides an optimal wavelength of light for treating circadian rhythm disorders. In the case of a multiple-wavelength device, the wavelength or combination of wavelengths of light can be easily selected as needed, and no unwanted wavelengths of light are delivered or need to be filtered.

Figure 3:
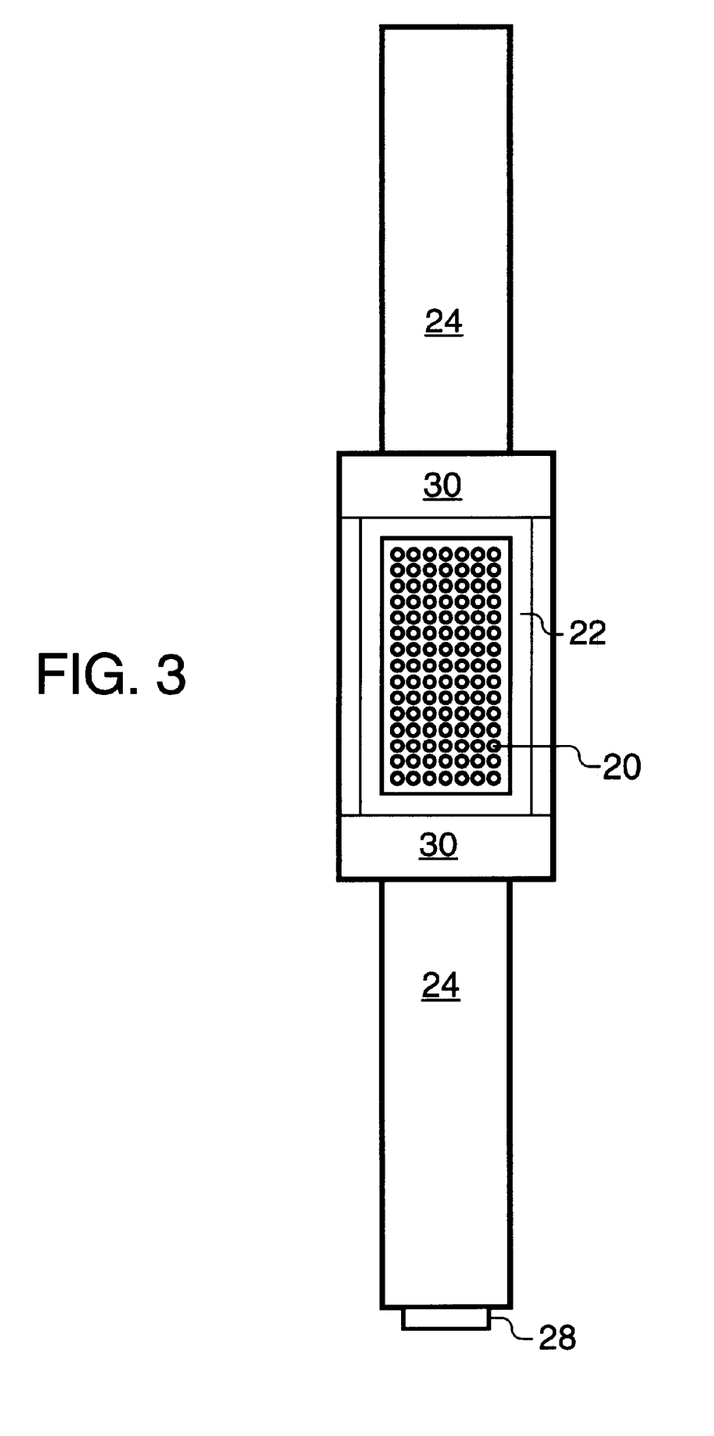
FIG. 3 is a front view of a body pad device according to the present invention.
Figure 4:
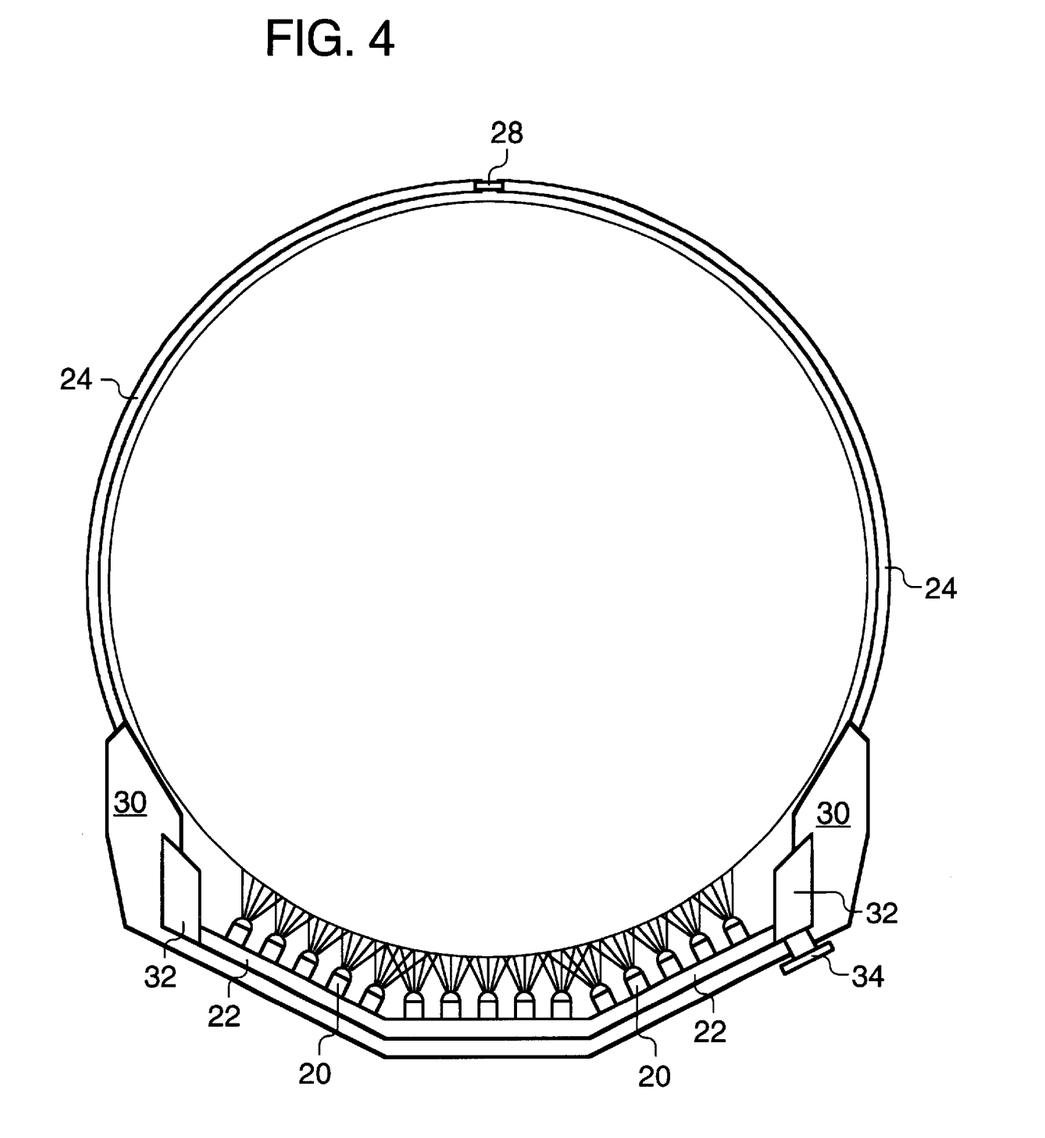
FIG. 4 is a top view of a body pad device according to the present invention.

FIGS. 3 and 4 show, respectively, a front view and a top view of a body pad device according to the present invention In contrast with all prior devices, this device is not designed to illuminate the retinas, but to illuminate the blood passing through the vascular tissue beneath the skin. As a result, this device can be used to treat circadian rhythm disorders while asleep, at rest, or at work, and without interfering in any way with vision or sleep patterns. In addition, the device can be completely hidden from the view of others and is entirely inconspicuous. Like the eyeglass-type device discussed above, this body pad device also enjoys the various advantages of using LED's to directly illuminate the subject.

As shown in the figures, an array of LED's 20 are arranged in a flexible or rigid mounting 22 attached to a fabric or other material 24 for securing the LED's near the skin 26 of a subject. The LED's are preferably GaN-based LED's with wavelengths in the blue to green portion of the spectrum. These LED's have high intensity and may be powered by low voltage (3 to 5 Volts DC). The LED's may be selected to have specific wavelengths and/or specific angular intensity distributions (e.g. broad beam or narrow beam). The mounting 22 preferably has a reflective surface to minimize the amount of light absorbed by the device and maximize the amount of light absorbed by the tissue. The material 24 may be an elastic closed loop or an open band that is tied, buttoned, snapped, or otherwise attached with a fastener 28 after wrapping around a portion of the body. The device may be comfortably worn around the head as a headband or inconspicuously as part of a hat. The device may also be worn is around the neck, arm, waist, or leg. In addition, several similar such devices can be used simultaneously and worn around different parts of the body, e.g. one on each leg. Because the device can be worn underneath or integrated with clothing, it is inconspicuous. Foam or other type of padding 30 can be used to increase comfort. The device has a small casing 32 that contains a small battery source, which preferably comprises several rechargeable or replaceable batteries.

A programmable or application-specific integrated circuit (ASIC) can be included, with appropriate controls 34 comprising buttons, switches and/or indicator lights. These controls allow the subject to adjust the timing and intensity of the LED treatment. If multiple different wavelength LED's are built into the pad, these controls can adjust the timing and relative intensity of the different wavelengths. Preferably, the LED's emit light in the blue to green range of the spectrum. Because the wavelength is selectable, specific wavelengths can be used separately or in combination for treating or studying specific disorders, and no unwanted wavelengths need be filtered or dissipated.

It will be appreciated that this body pad device enjoys a combination of many advantages over other devices and methods for treating circadian rhythm disorders. Most importantly, the present invention provides a device that does not interfere in any way with vision, and thus can be worn while asleep and can be worn completely out of the view of others, such as underneath clothes. In addition, the device is portable, light weight, durable, long-lasting, compact, comfortable, easy to use, inexpensive, effective, energy-efficient, and does not consume large amounts of power or dissipate large amounts of heat. In addition, the wavelength of light can be easily selected as needed, and no unwanted wavelengths of light are delivered or need to be filtered. Note that more than one such device can be worn at one time for increased effect.

Figure 5:
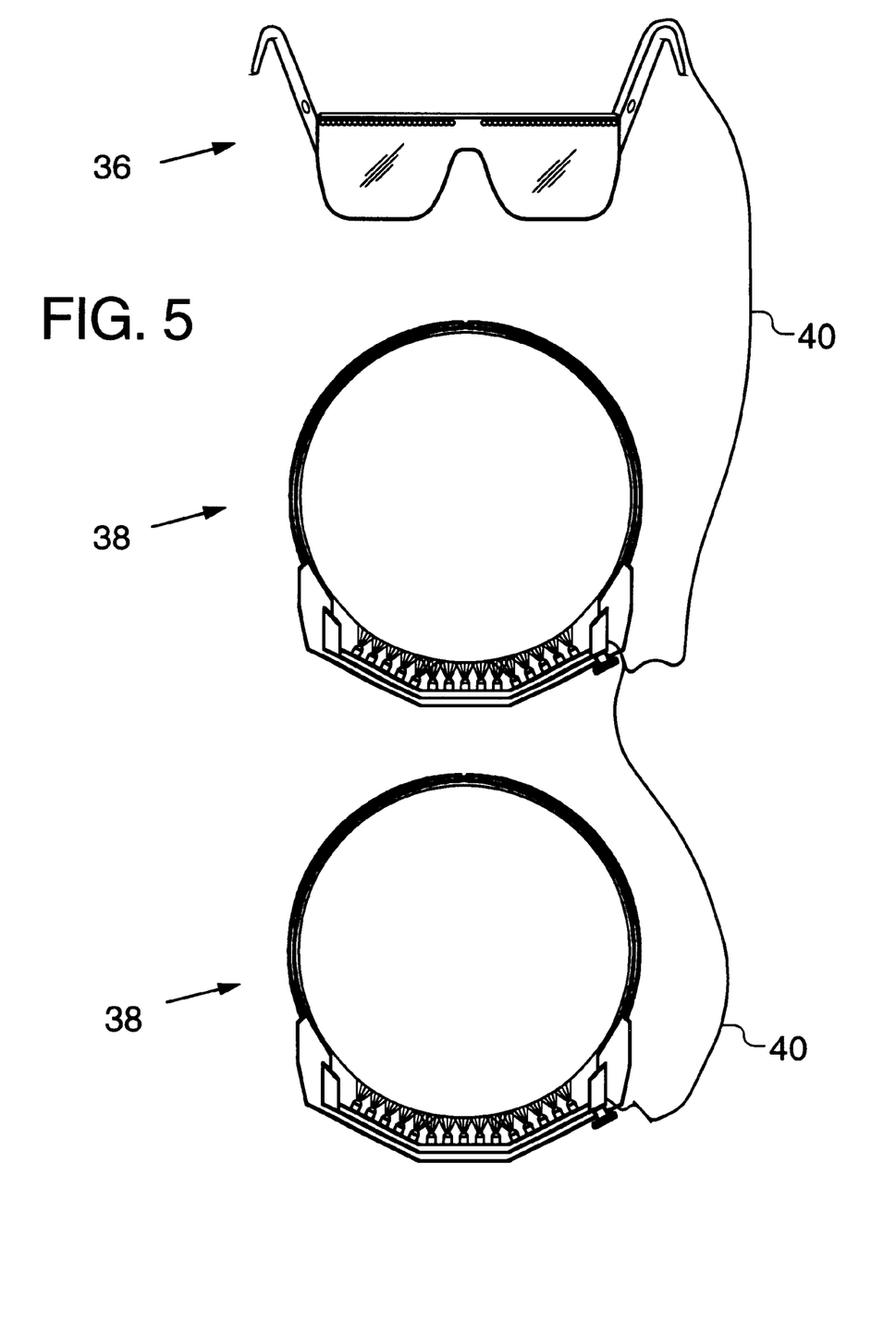
FIG. 5 is a schematic showing two types of devices used together according to the present invention.

FIG. 5 shows the eyeglass-type device 36 and the body pad device 38 used together according to the present invention. In this embodiment of the invention, these devices are used together in a method of treating circadian rhythm disorders. The glasses can be used to supplement one or more body pads. This combined mode of treatment is preferable while the subject is awake. The glasses can be removed if they interfere at all with vision, if the user goes to sleep, or if they attract unwanted attention to the subject. In such situations, the treatment typically continues with the body pads 38 alone. The two devices may be used separately, or may be connected together by a detachable thin electrical cord 40. The cord can connect the devices to a common power source, although preferably each pad has an independent power supply integrated into it. Typically, the electrical cord 40 will provide communication between the devices. Communication signals sent between the devices through the cord can be used to coordinate and control the multi-device treatment, For example, the microprocessor controller in a device can compensate for the inactivation of another device by the intensification of its LED light delivered, or by an increase in treatment duration.

Alternatively, this coordination can be performed manually by independently adjusting the separate devices. In this case, no cord 40 is necessary.

It will be appreciated that this combination of devices provides a method for treating circadian rhythm disorders that enjoys many advantages over other devices and methods. In addition to the advantages enjoyed independently by each of the devices, the coordinated and/or combined use of the two types of devices provides a synergy of effects, i.e. a treatment involving both illumination of the retina and the vascular tissue activates both the optic nerve and the chemical messengers in the blood to produce a combined effect that is more than the two independent modes of treatment alone. In addition, the simple combination of treatment modes also provides superior flexibility and effectiveness of treatment, depending on the activities and preferences of the subject.

General considerations and factors useful for diagnosing and treating circadian rhythm disorders are known in the art. Several parameters characterizing the light used for phototherapy affect the treatment efficacy, safety, and patient comfort. Such parameters include wavelength, light intensity, time and duration of treatment, angle of incidence, and distance of LED's from the subject. The patients may be allowed to vary some or all of the parameters in a method of the present invention. The wavelengths of light used are selected according to the resulting efficacy, safety, and comfort.

The present invention has important applications to convenient and inexpensive treatment of circadian rhythm disorders suffered by individuals such as night shift workers and jet travelers. In the case of jet lag, the body device is preferably worn at night in anticipation of a trip and programmed to automatically activate in the early morning hours or in the late night hours, depending on whether the anticipated direction of travel is east or west, respectively. In addition, the device can be used during travel, and after arrival at the destination to further reduce the effects of relocation. A few hours of illumination is sufficient in most cases, but may be increased or decreased depending on the specific diagnosis and/or treatment desired. A similar treatment would be used for a night-shift worker.

Before, during, and/or after the night-shift, the worker can be treated while awake, possibly combining the body pads with the eyeglasses, or while asleep. For treating SAD, one or both of the devices may be used for a few hours during the morning and/or evening hours of the day in order to compensate for reductions in environmental light levels.

Figure 6:
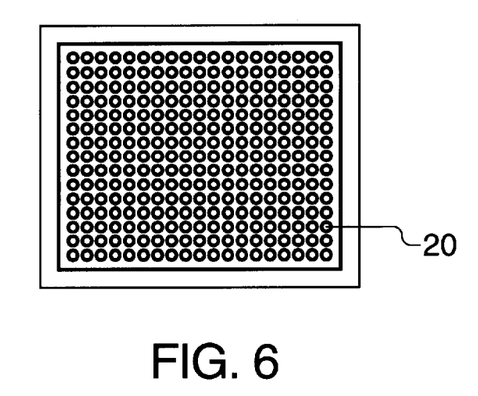
FIG. 6 is a front view of a panel illumination device according to the present invention.

The above embodiments of the invention are only a few examples of the many possible implementations of the invention. Many other embodiments and variations are considered in the scope of the present invention. For example, the LED's in the eyeglasses may be integrated within the arms of the glasses in addition to the portion of the frames surrounding the lenses. The device may also take the form of a small attachment to existing eyeglasses, such as one or more LED's mounted across the top of the subject's prescription glasses, or just to the side. It will also be appreciated that the LED's of the present invention are sufficiently intense that they can illuminate the retina through the closed eyelid. Thus, a night mask can be provided to deliver illumination to the retina while the eyes are closed during sleep or rest. Such a night mask may be used alone or in combination with the body pad device. Because of the superior intensity, frequency selectivity, and other advantages of LED's, a small and portable illumination panel device comprising an array of LED's, as shown in FIG. 6, can be used alone or in combination with the other devices of the invention. Such panels can be used to illuminate the eyes and/or the vascular tissue. A thin and portable panel the size of a small book, for example, can be easily carried with the subject and may comprise a clip or other attaching implement for positioning the panel near the subject.

Figure 7:
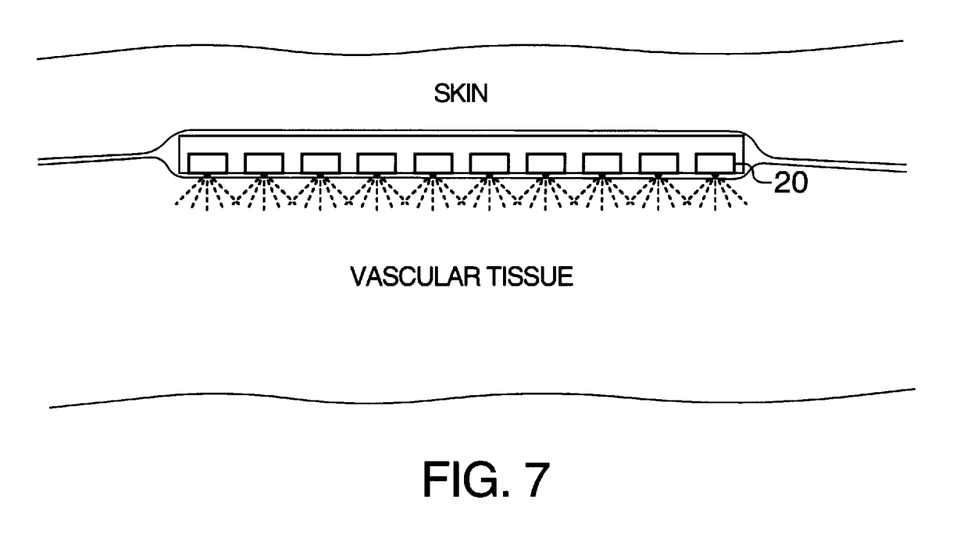
FIG. 7 is a side view of an implant device according to the present invention.

Another alternate delivery method is to implant a device comprising a collection of small chip-type LED's 20 within the body of the subject to deliver illumination directly to the vascular tissue without passing through the skin, as shown in FIG. 7. Due to their proximity to the vascular tissue and the elimination of losses due to absorption in the skin, such implants would not need to produce as much light to achieve the same effect as external devices. As a result, the implants could be smaller and more efficient. The implanted LED's could be powered by small batteries implanted with the LED'S, or by a power source external to the body and delivered through the skin by electrical induction, ultrasonic waves, or other means of wireless energy transmission.

It will also be appreciated that the blue LED's can be coated with phosphor to produce white LED's. These broader spectrum LED light sources have all the other advantages of the LED's, but in addition provide a white light that may be easier on the eyes while being also more natural and less conspicuous than the colored light sources. In specific applications where white light is required or preferable, the LED's used in the devices described above can be replaced or supplemented by such white LED's. These and many other variations will be evident to those skilled in the art. Accordingly, the scope of the invention is not to be construed to be limited by the details of the above illustrative embodiments, but by the following claims and their legal equivalents.

We claim:

1. A method for treating circadian rhythm disorders experienced by a subject, the method comprising:
   (a) illuminating the vascular tissue beneath the skin of the subject with light produced by a portable device worn by the subject, wherein the device comprises a plurality of light emitting diodes (LED's) positioned within 3 cm of and oriented toward the subject for illuminating the subject, a power supply connected to the LED's, and a control connected to the LED's; and
   (b) simultaneously illuminating the subject with light produced by an additional device worn by the subject.

2. The method of claim 1 wherein the LED's comprise LED's having wavelengths in the range from 420 nm to 575 nm.

3. The method of claim 1 wherein the LED's comprise chip-type LED's.

4. The method of claim 1 wherein the LED's comprise GaN-based LED's.

5. A method for treating circadian rhythm disorders experienced by a subject, the method comprising:
   (a) illuminating the subject with light produced by a portable device worn around a portion of the subject's body, wherein the device comprises a plurality of light emitting diodes (LED's) positioned within 3 cm of and oriented toward the subject for illuminating the subject, a power supply connected to the LED's, and a control connected to the LED's; and (b) simultaneously illuminating the subject with light produced by an additional device worn by the subject.

6. The method of claim 5 wherein the LED's comprise LED's having wavelengths in the range from 420 nm to 575 nm.

7. The method of claim 5 wherein the LED's comprise chip-type LED's.

8. The method of claim 5 wherein the LED's comprise GaN-based LED's.

9. A method for treating circadian rhythm disorders experienced by a subject, the method comprising:

illuminating the subject with light produced by a portable device worn by the subject, wherein the device comprises a plurality of light emitting diodes (LED's) positioned within 3 cm of and oriented toward the subject for illuminating the subject, a power supply connected to the LED's, and a control connected to the LED's; and simultaneously illuminating the subject with light produced by an additional device worn by the subject.

10. The method of claim 9, wherein the LED's comprise LED's having wavelengths in the range from 420 nm to 575 nm.

11. The method of claim 9, wherein the LED's comprise chip-type LED's.

12. The method of claim 9, wherein the LED's comprise GaN-based LED's.

* * * * *